United States Patent [19]

Sninsky et al.

[11] 4,374,927
[45] Feb. 22, 1983

[54] EXTRACHROMOSOMAL REGULATION OF EXPRESSION

[75] Inventors: John J. Sninsky, Mountian View; Stanley N. Cohen, Portola Valley, both of Calif.

[73] Assignee: The Board of Trustees of the Leland Stanford Jr. University, Stanford, Calif.

[21] Appl. No.: 237,555

[22] Filed: Feb. 24, 1981

[51] Int. Cl.$^3$ .................... C12P 21/00; C12P 21/02; C12N 15/00; C12N 1/20; C12N 1/00; C12R 1/19
[52] U.S. Cl. .................................. 435/68; 435/317; 435/70; 435/172; 435/849; 435/253
[58] Field of Search ................ 435/68, 172, 253, 317, 435/193, 183, 70

[56] References Cited

FOREIGN PATENT DOCUMENTS 467 7/1979 Fed. Rep. of Germany ...... 435/317

Primary Examiner—Alvin E. Tanenholtz
Assistant Examiner—J. Martinell
Attorney, Agent, or Firm—Bertram I. Rowland

[57] ABSTRACT

Microbiological methods, compositions and transformants are used for production of organic products for controlling cellular properties. Extrachromosomal elements are used which are subject to external modulation for production of a control element. The change in the amount of production of the control element allows for enhanced expression of a gene producing a poly(amino acid) product. The change in production of the control element allowing for enhanced gene expression of the product is accompanied by amplification of the product producing gene.

32 Claims, No Drawings

EXTRACHROMOSOMAL REGULATION OF EXPRESSION

BACKGROUND OF THE INVENTION

1. Field of the Invention

Hybrid DNA technology has already demonstrated the ability to produce products which heretofore were either not available or obtainable at extremely high cost and in relatively small amounts. Production of such proteins as human growth hormone, interferon, thymosin and others have already been announced as the forerunners of a large number of naturally occuring proteins as well as modified naturally occuring proteins which will have physiological effect. With the advent of the ability to make proteins, interest has arisen in expanding the type of product which can be produced, as well as the amount.

A number of situations would appear to put severe limitations on the efficiency, economics or ability to make a variety of products. Where a product is detrimental to the growth of the host microorganism, the cost of production of such products can become uneconomical. Similarly, in situations where the rate of production of a product of interest is off-set by the rate of its degradation, the yields may be uneconomically low. Also, where the product of interest is present in only an extremely small percentage of the total protein produced by the micro-organism host, so as to make isolation and purification a major problem, the economics may discourage development. Any one of these considerations can inhibit the production of a desired product and situations may be encountered whereby two or more of the above concerns may be combined.

It is therefore desirable to find new ways to produce products where previous experience has indicated that the products can only be difficultly produced, if at all, by microbiological techniques. Furthermore, there is continued interest in providing techniques which enhance the efficiency of production of products or allow for modulation of signals in a host cell to provide for the development of properties at will.

2. Description of the Prior Art

Uhlin, et al, Gene. 6 (1979) 91-106 describe plasmids with temperature-dependent copy number for amplification of cloned genes and their products. Bremer, et al, Molec. gen. Genet. 179, 13-20 (1980) describe production of a lethal product in a transformant from a structural gene on a plasmid. Bernard et al., Gene 5 (1979) 59-76 describes the use of a gene expressing a temperature-sensitive repressor controlling a lambda promoter coupled with structural genes. Heat induction is employed to regulate expression of the structural genes. Little, Molec. gen. Genet. 177, 13-22 (1979) describes production of a lethal protein product from a plasmid. Backman and Ptashne, Cell 13, 65-71 (1978) describe a strong promoter, namely the lac promoter. Hare and Sadler, Gene 3 (1978) 268-279 describe lac mutations resulting in enhanced repressor production.

SUMMARY OF THE INVENTION

Microbiological techniques, employing compositions and transformants, are provided for the production of difficulty obtainable poly(amino acids). Extrachromosomal elements are devised which can be controlled by an external modulator, either physical or chemical, to enhance or diminish the production of an organic chemical control element. The change in the amount of control element produced allows for enhanced expression of a gene, which gene is amplified concurrently with the enhanced expression. The combined enhanced expression and gene amplification allows for a burst of production of the product expressed by the gene influenced by the control element. The subject method finds particular application where the product of the gene subject to the control element is only capable of being produced in low yield, if at all.

DESCRIPTION OF THE SPECIFIC EMBODIMENTS

Microbiological methods are provided employing extrachromosomal elements for controlling the production of a desired product, normally temporal control by physical or chemical means. The method involves the use of an extrachomosomal element capable of replication in a microorganism host. The extrachromosomal element has a gene which is subject to control by an external modulator, which modulates the amount of expression product (control factor) of a gene on the extrachromosomal element. The control factor controls the expression of a second gene involved with production of a desired product in the host microorganism.

As a result of the change in concentration of the control factor in the host microorganism, expression of the gene is enhanced. The enhanced expression is accompanied by amplification of the product producing gene, so that one realizes enhanced production of the product, both as a result of the change in concentration of the control factor and the increase in the copy number of the product producing gene. This results in a production burst of the product.

Certain terms will be used throughout the specification. These will be defined here and discussed subsequently.

External modulator—chemical or physical means external to a host cell for regulating expression of a gene which expresses the control factor.

First regulatory system—components which together regulate expression of the gene expressing the control factor, the control factor producing gene. The first regulatory system includes at least the external modulator and a DNA sequence referred to as the first regulatory element, which controls expression of the control factor producing gene.

Control Factor—the molecular expression product of a gene, which product together with other components regulates expression of a structural gene which produces a desired poly(amino acid).

Second regulatory system—components which together regulate the expression of a structural gene producing a desired poly(amino acid) product, the product producing gene. The second regulatory system includes as components at least the control factor and a DNA sequence referred to as a second regulatory element which regulates expression of the product producing gene.

Extrachromosomal element (ECE)—extrachromosomal DNA capable of replication in a host and including besides a functioning replicon, the first regulatory element and the control factor producing gene.

Product Producing Element (PPE)—extrachromosomal DNA capable of replication in the same host as the ECE, including a runaway-replication-vector, a second regulatory element and the gene which expresses the poly(amino acid) product. In some instances the ECE and PPE may be the same extrachromosomal element, where all the necessary DNA elements are on the same continuous DNA chain.

The subject method is a microbiological method which can employ a wide variety of microorganisms as hosts. Microorganisms can include bacteria, fungi, e.g. yeast, protozoa, or algae. A large number of these microorganisms have already been used as hosts for introduction of foreign DNA employing phage, viral or plasmid vectors. Illustrative bacterial hosts include Enterobacteriaciae, Streptococci, Staphylococci, Bacilli, Corynebacteri, Actinmycetes, etc. Fungi include Sacchromyces, Elastomyces, Candida, Asperigillus, etc. Protozoa include Mastigophora, Sporozoa, Cnidosporida, Ciliophora, etc. Algae include Microspora, Chlamydomas, Oocystis, Euglena, etc.

The extrachromosomal element (ECE) will be a DNA segment, either linear or circular, which may change its form in the cell, becoming circularized and supercoiled. The ECE will be capable of replication, and has at least one sequence capable of transcription and usually expression in the microorganism host. The ECE will have at least one DNA sequence whose expression can be modulated by an external modulator, either directly or indirectly, and provides for production of the control factor.

The ECE will be comprised of a replicon, that is, a DNA sequence, which may be contiguous or non-contiguous, providing the necessary sequences for replication of the ECE. In addition, the ECE will have a DNA sequence (first regulatory element) which provides for the regulation and production of a product referred to as the control factor. Other DNA sequences which may be included in the ECE include markers which allow for selection of the ECE during preparation and cloning of the ECE. There may be more than one marker, which markers are primarily for convenience in the preparation and isolation of the ECE. More than one replicon may be present, where it is desirable to replicate the ECE in different hosts which require different replication systems.

Also present on the ECE is a DNA sequence susceptible to regulation by the external modulator, defined as the first regulatory element. The first regulatory element controls expression of the DNA sequence referred to as the control factor producing gene.

The replicon(s) may be derived from plasmids, chromosomes, viruses, or may be synthetically produced. The source of the replicon is not significant, so long as it allows for replication in the target host, and, as appropriate, in a cloning host. Depending on the amount of control factor required a runaway-replication-vector may be employed, particularly where the control element stimulates expression.

The regulatory sequences will normally be origins, promoters, initiators, start and stop sites, and the like. These may be present accompanying the gene when obtained from a particular source or may be present on the replicon to which the gene is joined. The manner in which they exercise their regulatory function will be discussed subsequently.

Another portion of the ECE is the first regulatory element which regulates the gene which produces the control factor. The first regulatory element can function in a variety of ways. The first regulatory element must be sensitive to control by the external modulator, which modulation results in a change in the amount of expression product of the gene(s) producing the control factor.

The first regulatory system is sensitive to external modulation by physical or chemical means and includes such means as part of the system. Physical means can include changes in temperature, either increases or decreases, light, or other physical phenomenon to which a regulatory gene may be sensitive, either directly or indirectly. Chemical means can include various effectors, normally small molecules under 1,200 daltons, some of which are known as inducers or corepressors, such as urocanate, nitrate, $\alpha$-acetolactate, amino acids e.g. isoleucine, $\beta$-allolactose, and the like. Where physical external modulation is involved, one need only provide for a relatively rapid change in the temperature of the nutrient medium or in the light flux of a particular range of wavelengths applied to the microorganisms in the nutrient medium. Where a chemical external modulator is employed, one can achieve this by rapidly adding the particular chemical compound to the nutrient medium to provide for rapid transfer of the effector compound across the membrane into the cytoplasm and nucleus.

The modulation of expression of the control factor producing element can be achieved in a variety of ways. Modulation of expression of the control factor producing element on a plasmid can be achieved by a reduction in the copy number of the plasmid, so that the first regulatory element reduces the amount of replication of the plasmid. Within a few generations of the microorganism host, there will be a substantial diminution of the number of plasmids present in the host having the first regulatory element and control factor producing gene.

Rather than controlling replication, the regulatory system can be involved in repression or induction, so that transcription of the control factor producing gene can be enhanced or repressed. Thus, the regulatory system may include an operator or an initiator and a structural gene producing a repressor or activator protein. Such structural gene will normally be part of the ECE. Regulatory elements may also be sites which act as DNA polymerase or RNA polymerase start sites, which are sensitive to external modulation, normally due to mutant types of polymerases. tRNA supressors may be used for regulation to supress a nonsense mutation which prevents expression of the control factor.

Depending upon whether the control factor is an activator or a repressor of the gene expressing the desired product, the regulatory gene will act to either enhance or diminish transcription of the gene producing the control factor. Thus, if one wishes to have a large amount of control factor present in the host microorganism, it will be desirable to either or both increase (1) the rate of expression of the gene producing the control factor, and (2) the copy number of the gene producing the control factor. If one wishes a small amount of control factor present in the host microorganism, then it is desirable to diminish the rate of expression, as well as the copy number.

The control factor can be a wide variety of proteinaceous or non-proteinaceous products. As proteinaceous products, the control factor can function as a repressor, activator, enzyme, or protein serving a specific function involved with expression, which function enhances the expression of the gene producing the desired product. The function of repressors and initiators is well known and need not be expatiated upon here. See for example, Biological Regulation and Development, Volume I, Gene Expression, ed. Robert F. Goldberger, Plenum Press, New York and London (1979).

Where inhibition results from the control factor, the external modular would act on the first regulatory element to effect a reduction in transcription of the control factor producing gene. By contrast, where an activation is involved, the external modulator would act on the first regulatory element to effect an enhancement. Where an enzyme is involved, the enzyme can be involved in the production or destruction of an inducer or corepressor employed in combination with endogenous activator or repressor.

As already indicated, the first regulatory element can also function, not by directly activating or inhibiting expression of the gene expressing the control factor, but by increasing or diminishing the copy number of the gene expressing the control factor. In this instance, this will normally be a function of inhibiting DNA polymerase replication of the ECE.

Other proteins which might be employed are sigma factors which are specific for a particular RNA polymerase site associated with the product producing gene; antiterminating factors, etc. Therefore, there can be a wide variety of techniques employed for enhancing the expression of the desired product.

A preferred system employs a first regulatory system having the following components. The external modulator is physical and preferably temperature. The control factor inhibits production of the desired product and an increase in temperature results in a reduction in production of the control factor. The first regulatory element modulates the expression of the control factor producing gene without production of a protein, desirably by changing binding characteristics with change in temperature.

The second regulatory element regulating the gene expressing the desired product will be complementary to the nature of the control factor. Therefore, with a repressor control factor, the second regulatory element will be an operator; with an activator control factor, the second regulatory element will be an initiator; etc.

In accordance with this invention there will be substantial amplification of the gene producing the desired product at the time when the change in production of the control factor results in enhanced production of the desired product. Where the control factor inhibits expression, it will be desirable that the copy number of the control factor producing gene either remains the same or is reduced. However, where the control factor is involved in enhancement of expression of the product producing gene, it will be desirable that the copy number of the control factor producing gene be amplified concurrently with the copy number of the product producing gene. The amplification of the two genes may be as a result of the same or different external influence, usually the same, and either physical or chemical.

For inhibitory control factors there will be a number of desiderata. Included among these are that the control factor has a relatively short half-life. That is, at the time when enhanced expression of the product producing gene is desired, there should be a rapid reduction in the amount of the control factor. Another property is that relatively low concentrations of the control factor should be effective in inhibiting expression of the desired product, so that there should be substantially no production of the desired product under inhibiting conditions.

For activating control factors, considerations will include the half-lives of the mRNA for the control factor and the control factor, the amount of control factor necessary for the required level of the desired product, the leakiness of the system under inhibiting conditions for the production of the poly(amino acid) product and the rapidity with which the desired level of control factor can be reached.

In devising the ECE, an appropriate replicon can be chosen having one or more desired markers. The replicon may be one which allows for replication in a single host or a plurality of hosts. The advantage of having a replicon which allows for replication in a plurality of hosts is that the ultimate host may be inconvenient for cloning. The first regulatory system may act directly or indirectly on the control factor producing zone. Indirect control envisions changes in the copy number of the ECE. Direct control will normally be inability of transcription or translation. Various techniques for direct control have been described previously. The next component of the ECE is the control factor producing gene.

The plurality of functional DNA sequences indicated above may be derived from naturally occurring sources or synthesized, or combinations thereof. The sequences may be joined in accordance with known techniques to provide the ECE.

The second regulatory system is comprised of the control factor and the regulatory element controlling expression of the product producing gene. The regulatory element and product producing gene will be extrachromosomal and will be part of the product producing element (PPE). Various regulatory elements may be employed which may be switched from an off condition, where gene expression does not occur, to an on position, where gene expression does occur. While positive or negative regulation may be involved, negative regulation is preferred, where expression is repressed by the control factor. The extrachromosomal PPE can be prepared in the same manner as described for ECE. Illustrative regulatory sequences include the regulatory sequences of the lacZ gene, trp operon, lambda phage and the like.

There will also be a third regulatory system, which results in rapid amplification of the product producing gene. This type of regulatory system is part of what is known as a runaway-replication vector. Uhlin, et al, supra. Thus, by employing a runaway-replication vector in the preparation of the plasmid which incorporates the regulatory sequence of the second regulatory system and the product producing gene, not only can expression of the product producing gene be enhanced by the presence or absence of the control factor, but by amplification of the product producing gene, one can achieve an enormous burst in activity. The runaway-replication vector is activated, usually physically by a temperature change. Desirably, temperature is the external modulator, so that enhanced expression and amplification are under the same control.

Preferably the control factor will be an inhibitor, rather than activator, since where amplification is involved, one would have to amplify both the product producing gene as well as the control factor. With inhibition, the opposite is true, in that one would only amplify the product producing gene and maintain or diminish the amount of control factor.

In order to produce the desired product, one would introduce by conventional means into an appropriate microorganism host the ECE and PPE. The replicons of the ECE may be the same or different, normally being different. However, where the control factor is an activator, it would be desirable to use a runaway-replication-vector with both the ECE and the PPE.

The resulting transformants will be grown in an appropriate nutrient medium. One then grows the organisms to high density, generally greater than $10^6$ cells/ml, preferably greater than $10^7$ cells/ml, the limitation being on the ability to provide sufficient nutrients to the cells, remove inhibitory products, and subject the cells to the external modulator in a reasonably uniform manner. Therefore, as improved methods for growing cells are developed, greater cell densities will be achievable.

Once the desired density has been achieved, the cells will be subjected to the external modulator. In a situation where a change in temperature is the external modulator, the change in temperature can be achieved by rapidly cooling, heating, or introducing a nutrient medium of a different temperature. Similarly, with the external modulator as a chemical, by replacing the nutrient medium or employing a flowing stream of nutrient, the concentration of the external modulator in the nutrient medium can be rapidly changed. The process can be batch or continuous. Conveniently, once the cells have reached a high density, they can be diluted into a nutrient medium while being subjected to the external modulator.

Once the desired product is produced, it may be isolated from the nutrient medium in accordance with known ways. In most situations, the desired product will be produced in at least about 0.2 percent of the total protein produced by the cell, usually at least about 1.0 percent, desirably at least about 2 percent, and preferably at least about 5 percent of the total protein produced by the cell.

Normally, the time required to go from the application of the external modulator to the cells to the maximum rate of production or termination of production of product will be under 12 hours, usually under six hours and preferably under three hours.

A wide variety of products are of interest, particularly polypeptides and proteins-(poly(amino acids)). Of great interest are mammalian hormones and regulatory factors, such as interferon e.g. immune interferon, thymosin, human growth hormone, chorionic gonadotropin, lymphokines, regulatory factors e.g. erythropoietin, as well as other proteins or fragments thereof, such as beta-lipotropin, beta-endorphin, and the like. Other products of interest include enzymes, such as hydrolases, oxidoreductases, isomerases, transferases, and ligases or sythetases. Of course, the enzyme may not be the end product, but may be produced in order to react with a compound in the nutrient medium to transform the compound to provide a non-proteinaceous product.

While for simplicity, the description has been confined to a system which regulates a single gene or operon as the second regulatory system, it should be understood that the system could be extended further to have a cascading effect. Therefore, one could provide situations where a plurality of DNA sequences are employed to regulate and express products sequentially. This would be particularly advantageous, where one wished to have timed intervals of production of products to lead to a finally desired product. Furthermore, there may be one or more copies of each of the DNA elements, so long as each of the copies has the same interrelationships as described for a single copy.

With some regulatory systems, the external modulator may control any of the regulatory components in the first and second regulatory systems. For example, the control factor can be a temperature sensitive repressor and/or the second regulatory element could be a temperature sensitive operator. Thus upon a change in temperature expression of the product producing gene could be stimulated.

The following examples are offered by way of illustration and not by way of limitation.

EXPERIMENTAL

Plasmid pPM 103 is a temperature-sensitive replication mutant of pSC101 and is cured efficiently in approximately five cell doublings, which is the number of cell doublings necessary for efficient amplification of the runaway plasmids which will be described subsequently. pPM103 has a copy number of about four to seven. The lacI$^q$ gene has a promoter mutation in lacI that allows synthesis of ten-fold more repressor than the wild type. The plasmid pHIQ6 is a pMB9 derivative that contains an EcoRI fragment which carries lacI$^q$. The plasmids pHIQ6 and pPM103 will both cleave with EcoRI and are ligated before transformation into an E. coli C600 strain which harbors pJJS300. Plasmid pJJS300 is a pBR322 derivative carrying the lac promoter and operator region found in 25-50 copies per cell.

The transformants were selected on Ap, Tc, Xgal indicator plates at 30° C. On these plates, the strain bearing pJJS300 is normally blue because the lac repressor is titrated away from the chromosomal lacZ gene and thereby inducing beta-galactosidase, causing a cleavage of the chromogenic substrate. Ap$^r$, Tc$^r$ white colonies were selected from these plates indicating the lac$^q$ was present in the same cell as pJJS300 preventing lacZ induction. The above colonies were picked onto Tc plates and incubated at 42° C. to identify those containing a temperature-sensitive plasmid.

A representative transformant from the screening was chosen and DNA was isolated to verify the construction by endonuclease cleavage analysis. Agarose gel electrophoresis was performed on the EcoRI digest of this DNA using pHIQ6, pPM103, and pJJS300 as markers. The pPM103 derivative that carried the lac$^q$ gene was designated pJJS1002. Separation of pJJS300 and pJJS1002 was achieved by transformation into E. coli MC1000.

The construction of a runaway-replication vector derivative containing a lac controlled heterologous gene involved the introduction of (1) an antibiotic resistance marker; (2) the lac promoter-operator; and (3) a heterologous gene regulated by the lac promoter, onto pKN402 (Uhlin et al., supra). Sm$^r$/Sp$^r$ was the chosen antibiotic resistance since it is carried on a HindIII fragment that contains a BamHI site. Since the BamHI site is not within the Sm$^r$/Sp$^r$ gene, a purified SauIIIA fragment from pJJS300 that carried the lac promoter-operator was able to be inserted. Chloramphenicol acetyltransferase (CAT) was the heterologous gene chosen as exemplary, because a SauIIIA from pACYC 184 contains the coding sequence for this gene, but not its promoter and a convenient assay for activity is available.

After it was shown that the derivatives of pPM103 and pKN402 have identical temperature-dependent replication properties as their respective parent plasmids, an E. coli MC1000 strain was constructed that contained both pJJS1002 and pJJS1011.

pJJS1011 is derived from the runaway-replication vector pKN402. pDPT427 contains the copy number mutant replicon of pRR12 and confers resistance to both spectinomycin ($Sp^r$) and chloramphenicol ($Cm^r$). A HindIII fragment of the plasmid contains the $Sp^r$ from pRR12. HindIII cleaved pDPT427 and pKN402 were ligated and $Sp^r$ transformants of E. coli MC1000 were selected at 30° C. A Cls and a temperature-sensitive phenotype at 42° C. were obtained by screening. The resulting plasmid designated pBEU27, from a representative transformant, was digested with BamHI and ligated to a 410 db SauIIIA fragment from pJJS300 that contains the lacZ promoter-operator region and $Sp^r$. Blue transformants were selected from Sp-Xgal plates. DNA of a representative transformant was isolated and identified as pJJS1010. The sequence of the SauIIIA sites of this fragment are such that insertion into a BamHI cleaved molecule regenerates a BamHI site only at the downstream site, thereby allowing the determination of the orientation of insertion by a double digest with HindIII and BamHI. Cleavage of pJJS1010 with BamHI and ligation with a purified 1000 bp SauIIIA fragment from pACYC184 that contains the coding sequence for $Cm^r$, but not the promoter, and subsequent transformation resulted in $Sp^rCm^r$ colonies. All $Cm^r$ transformants contain the $Cm^r$ fragment oriented such that expression is controlled by the lac regulatory region. A representative plasmid was chosen and designated pJJS1011. The sequence of the SauIIIA of the $Cm^r$ fragment does not allow the regeneration of a BamHI site.

After screening, optimal conditions for curing and amplification in the system were found to be a temperature shift of 30° C. to 43° C. growing in rich media containing spectinomycin.

Amplification is carried out by initially inoculating an 8 ml L-broth standing culture bacterial strain and plasmid(s). Growth at 30° C. is monitored and is kept less than $1 \times 10^8$ cells/ml. For 10 hrs the cells are kept at exponential phase in a shaking 30° C. culture for 10–15 generations. Dilution ($50 \times$) into prewarmed (43° C.) L-Broth of this culture initiates amplification. Following 4–5 generations (~150 min) at 43° C., the cultures are rapidly chilled on ice and incubated in a 30° C. shaking waterbath for an additional 45 min.

The following table indicates the results obtained from the amplification study.

TABLE I

GENE PRODUCT AMPLIFICATION OF CHLORAMPHENICOL ACETYLTRANSFERASE (CAT)

| Temperature | Time after temperature shift | Specific activities of $CAT^a$ | | |
|---|---|---|---|---|
| | | pJJS1011 | pJJS1011 + pJJS1002 | $pACYC184^c$ |
| 30° C. | 0 | 10 | 1 | 360 |
| 43° C. | 75 | 28 | 7 | 360 |
| | 150 | 116 | 85 | 360 |
| 43° C.→30° C.$^b$ | 195 | 328 | 317 | 360 |

$^a$Specific activities expressed relative to cells carrying pJJS1002 and pJJS1011 at 30° C.
$^b$Incubation for 150 min at 43° C. and then another 45 min at 30° C.
$^c$Corrected for instability of plasmid.

As can be seen from the above table, pJJS1002 allows for a ten-fold reduction in the expression of CAT from pJJS1011 at 30° C. The temperature-dependent induction and amplification of lac regulated CAT allows for an approximately 300-fold increase in the amount of CAT expressed.

A polyacrylamide gel analysis was made of the proteins produced at 30° C. versus 43° C. At 30° C., CAT is not visibly detectible by Coomasie blue stain. However, following induction and amplification, it became one of the most prominent proteins in the cell. It is estimated that the quantity of CAT is at least 1% of the total protein of the cell.

A pulse labeling experiment was carried out in order to determine the relative rate of expression of the induced amplified lac control CAT compared to CAT from pACYC184. Densitometric scanning of an autoradiogram indicated that the quantity of CAT produced from E. coli MC1000 harboring pJJS1002 and pJJS1011 after 120 minutes at 40° C. is five times greater than the CAT synthesized from pACYC184.

The autoradiogram was prepared by labeling whole cell proteins with $S^{35}$-methionine. The labeling was performed by harvesting cells at 120 min after a temperature shift from 30° C. to 43° C. and then resuspending in equal volume of Difco Methionine Assay Medium, followed by incubation for 20 min at 43° C. labeling of the cells by adding labeled methionine (10 $\mu$Ci/ml) for 5 min, cold chased by adding methionine at 100 $\mu$g/ml for 2 min and harvesting and fractionation. The cells were washed at specified times with 10 mM Tris (pH 7.4)-1 mM EDTA before being suspended in Laemmli sample buffer and boiled for 5 min. Whole cell proteins were fractionated on 12.75% sodium dodecylsulfate-polyacrylamide gels by the method of Laemmli, (1970) Nature 227, 680–685. After treatment with EnHance (New England Nuclear Co.) using conditions suggested by the vendor, the gel was dried and exposed to X-ray film. Molecular weight standards were run, demonstrating the enhanced synthesis of CAT at 43° C.

It would be expected that a pulse-labeling after the 30° C. incubation following the 43° C. induction and amplification would show an even greater increase. The concomitant induction and amplification of lac controlled heterologous genes using the plasmids described here allows for a burst of synthesis of the desired protein. In accordance with the subject invention, methods and compositions are provided for production of proteins under controlled conditions, where the proteins are synthesized on demand. The desired product may be the protein, or where the protein is an enzyme, a non-proteinaceous product of the enzyme.

The subject invention finds particular application in situations where the product has a detrimental effect on cell growth, the extreme situation being a lethal product. Another situation where the subject invention finds ready application is where the product is subject to proteolytic degradation. With the subject invention, proteases may be overwhelmed by the large amount of protein produced, which may then be rapidly scavenged from the nutrient medium, where the protein is excreted or the cells may be lysed and the protein isolated. A third situation is where only low expression is achieved of the desired protein which can be the result of many factors, including poor orientation between regulatory signals and the structural gene. The subject invention therefore provides an efficient and economic way for overcoming constraints on the use of microbiological techniques for the production of a wide variety of products.

Although the foregoing invention has been described in some detail by way of illustration and example for purposes of clarity of understanding, it will be obvious that certain changes and modifications may be practiced within the scope of the appended claims.

What is claimed is:

1. A method for producing a poly(amino acid) product on demand, said method comprising:
   (a) growing to a high density transformant microorganism host cells having at least one extrachromosomal element capable of replication in said host cells which includes:
   (1) an activatable runaway-replication vector,
   (2) components of a first regulatory system comprising a first regulatory element subject to control by an external modulator, wherein said first regulatory element regulates a gene producing a control factor,
   (3) components of a second regulatory system comprising a second regulatory element, subject to control by said control factor, wherein said second regulatory element regulates a gene producing a poly(amino acid) product,
   (4) a gene expressing a poly(amino acid) product replicated in conjunction with said runaway-replication-vector,
   (5) a gene expressing a control factor;
   (b) subjecting said cells to an external modulator which modulates expression of said control factor producing gene in a direction enhancing expression of said product producing gene, while activating said runaway-replication vector, where enhanced expression and amplification of said product producing gene occurs with enhanced production of said poly(amino acid).

2. A method according to claim 1, wherein said runaway-replication vector is activated by a change in temperature.

3. A method according to claim 2, wherein said external modulator is a change in temperature.

4. A method according to claim 2, wherein said external modulator is a low molecular weight organic compound.

5. A method according to any of claims 1, 2 or 3, wherein said control factor inhibits expression of said product producing gene.

6. A method according to claim 5, wherein said control factor is a repressor and said second regulatory element is an operator.

7. A method according to any of claims 1, 2 or 3, wherein said control factor stimulates expression of said product producing gene.

8. A method according to any of claims 1, 2 or 3 where said first and second regulatory elements are on separate extrachromosomal elements, and also included is a replicon which regulates replication of said first regulatory element and said control factor producing gene.

9. A method according to any of claims 1, 2 or 3, wherein said poly(amino acid) inhibits the growth of said host cell.

10. A method according to any of claims 1, 2 or 3, wherein said poly(amino acid) is rapidly degraded in said host cells.

11. A method for producing a poly(amino acid) product on demand, said method comprising:
    (a) growing to a high density transformant microorganism host cells having two extrachromosomal elements capable of replication in said host cell, wherein a first extrachromosomal element includes:
    (1) components of a first regulatory system comprising a first regulatory element subject to control by an external modulator, wherein said first regulatory element regulates a gene expressing a control factor; and
    (2) a gene expressing a control factor; and a second extrachromosomal element includes:
    (1) an activatable runaway-replication vector;
    (2) components of a second regulatory system comprising a second regulatory element subject to control by said control factor, wherein said second regulatory element regulates a gene expressing said poly(amino acid) product; and
    (3) a gene expressing said poly(amino acid) product;
    (b) subjecting said cells to said external modulator which modulates expression of said control factor producing gene in a direction enhancing expression of said product producing gene, while activating said runaway-replication vector, where enhanced expression and amplification of said product producing gene occurs with enhanced production of said poly(amino acid).

12. A method according to claim 11, wherein said runaway-replication vector is activated by a change in temperature and said external modulator is a parallel change in temperature.

13. A method according to any of claims 11 or 12, wherein said control factor inhibits expression of said product producing gene.

14. A method according to claim 13, wherein said control factor is a repressor and said second regulatory element is an operator.

15. A method according to any of claims 11 or 12, wherein said poly(amino acid) product is an enzyme.

16. A microorganism cell having at least one extrachromosomal element capable of replication in said cell which includes:
    (1) an activatable runaway-replication vector;
    (2) components of a first regulatory system comprising a first regulatory element subject to control by an external modulator, wherein said first regulatory element regulates a gene producing a control factor;
    (3) components of a second regulatory system comprising a second regulatory element subject to control by said control factor, wherein said second regulatory element regulates a gene producing a poly(amino acid) product;
    (4) a gene expressing said poly(amino acid) product replicated in conjunction with said runaway-replication vector,
    (5) a gene expressing a control factor.

17. A cell according to claim 16, wherein said runaway-replication vector is activated by a change in temperature and said external modulator is a parallel change in temperature.

18. A cell according to any of claims 16 or 17, wherein (2) is on a first extrachromosomal element and (1), (3) and (4) are on a second extrachromosomal element.

19. A cell according to claim 18, wherein said control factor inhibits expression.

20. A cell according to claim 18, wherein said poly(amino acid) is an enzyme.

21. A method for producing a poly(amino acid) product on demand, said method comprising:
(a) growing to a high density transformant microorganism host cells having at least one extrachromosomal element capable of replication in said host cells which include:
(1) an activatable runaway-replication vector;
(2) components of a first regulatory system comprising a first regulatory element regulating a gene producing a control factor;
(3) a gene expressing a control factor;
(4) components of a second regulatory system comprising a second regulatory element, subject to control by said control factor, wherein said second regulatory element regulates a gene producing a poly(amino acid) product wherein said control factor is a component of said second regularoty system;
(5) a gene expressing a poly(amino acid) product replicated in conjunction with said runaway-replication vector;
wherein at least one of said first and second regulatory systems is subject to control by an external modulator;
(b) subjecting said cells to an external modulator which modulates at least one of said first and second regulatory systems in a direction enhancing expression of said product producing gene, while activating said runaway-replication vector, wherein enhanced expression and amplification of said product producing gene occurs with enhanced production of said poly(amino acid).

22. A method according to claim 21, wherein said external modulator controls said second regulatory system.

23. A method according to claim 22, wherein said external modulator is temperature.

24. A method according to claim 22, wherein said control factor is a repressor and said second regulator element is an operator.

25. A method according to claim 24, wherein at least one of said repressor and operator is temperature sensitive.

26. A method according to claim 25, wherein said repressor is expressed constitutively.

27. A microorganism cell having at least one extrachromosomal element capable of replication in said cell which include:
(1) an activatable runaway-replication vector;
(2) components of a first regulatory system comprising a first regulatory element which regulates a gene producing a control factor;
(3) components of a second regulatory system comprising a second regulatory element subject to control by said control factor, wherein said second regulatory element regulates a gene producing a poly(amino acid) product, and said second regulatory system includes said control factor;
(4) a gene expressing said poly(amino acid) product;
(5) a gene expressing said control factor;
wherein at least one component of said first and second regulatory systems is subject to control by an external modulator.

28. A cell according to claim 27, wherein said control factor is a repressor and said second regulatory element is an operator.

29. A cell according to any of claims 27 or 28, wherein said external modulator is temperature.

30. A cell according to claim 27, wherein (2) and (5) are on one extrachromosomal element and (1), (3) and (4) are on a second extrachromosomal element.

31. A cell according to claim 30, wherein said external modulator controls at least one component of said second regulatory system.

32. A cell according to claim 31, wherein said external modulator is temperature.

* * * * *